US011260360B2

United States Patent
Zhang et al.

(10) Patent No.: US 11,260,360 B2
(45) Date of Patent: Mar. 1, 2022

(54) MICROENCAPSULATION

(71) Applicant: Encapsys, LLC, Appleton, WI (US)

(72) Inventors: Hanwei Zhang, Appleton, WI (US); Todd Arlins Schwantes, Lena, WI (US)

(*) Notice: Subject to any disclaimer, the term of this patent is extended or adjusted under 35 U.S.C. 154(b) by 0 days.

(21) Appl. No.: 16/657,206

(22) Filed: Oct. 18, 2019

(65) Prior Publication Data

US 2020/0122110 A1   Apr. 23, 2020

Related U.S. Application Data

(60) Provisional application No. 62/747,298, filed on Oct. 18, 2018.

(51) Int. Cl.
*B01J 13/16* (2006.01)
*C11D 3/37* (2006.01)
*D06M 23/12* (2006.01)
*A61K 8/11* (2006.01)
*C11D 3/50* (2006.01)

(52) U.S. Cl.
CPC ............. *B01J 13/16* (2013.01); *A61K 8/11* (2013.01); *C11D 3/373* (2013.01); *C11D 3/505* (2013.01); *D06M 23/12* (2013.01)

(58) Field of Classification Search
None
See application file for complete search history.

(56) References Cited

U.S. PATENT DOCUMENTS

| 8,937,477 B2 | 1/2015 | Murayama |
| 10,485,739 B2 | 11/2019 | Yan |
| 2017/0113200 A1* | 4/2017 | Zhang ............... A61K 8/87 |
| 2017/0216163 A1* | 8/2017 | Feng ............... A61K 8/8158 |

FOREIGN PATENT DOCUMENTS

| WO | 2017074998 | 6/2017 |
| WO | 2016061440 | 4/2019 |

* cited by examiner

*Primary Examiner* — Jeffrey D Washville
(74) *Attorney, Agent, or Firm* — Benjamin Mieliulis

(57) ABSTRACT

An improved process of making a benefit agent delivery particle and an improved microcapsule made by such process are disclosed. The process comprises the steps of providing a first composition of water phase 1, water phase 2, water phase 3 and an oil phase, where a water phase multifunctional (meth)acrylate monomer is selected to have a hydrophilicity index of least 25, or even at least 30 and the oil phase multifunctional (meth)acrylate monomer has a hydrophilicity index of 25 or less, or even 20 or less. The water phases comprise water, initiator, a water-soluble or dispersible amine(meth)acrylate or hydroxyl(meth)acrylate, a multifunctional (meth)acrylate and one water phase comprises water, carboxyalkyl(meth)acrylate and a base or quaternary ammonium acrylate. Water phases are combined to prereact the hydroxy- or amine(meth)acrylate and the multifunctional (meth)acrylate to form a multifunctional hydroxyl-amine(meth)acrylate pre-polymer. The pre-polymer is combined with the remaining water phase and an emulsion is formed by emulsifying under high shear agitation, an oil phase comprising a multifunctional (meth) acrylate monomer and a benefit agent core material thereby forming a wall surrounding the benefit agent core material.

16 Claims, 3 Drawing Sheets

MICROENCAPSULATION

Various processes for microencapsulation, and exemplary methods and materials are set forth in Schwantes (U.S. Pat. No. 6,592,990), Nagai et al. (U.S. Pat. No. 4,708,924), Baker et al. (U.S. Pat. No. 4,166,152), Wojciak (U.S. Pat. No. 4,093,556), Matsukawa et al. (U.S. Pat. No. 3,965,033), Matsukawa (U.S. Pat. No. 3,660,304), Ozono (U.S. Pat. No. 4,588,639), Irgarashi et al. (U.S. Pat. No. 4,610,927), Brown et al. (U.S. Pat. No. 4,552,811), Scher (U.S. Pat. No. 4,285,720), Jahns et al. (U.S. Pat. Nos. 5,596,051 and 5,292,835), Matson (U.S. Pat. No. 3,516,941), Chao (U.S. Pat. No. 6,375,872), Foris et al. (U.S. Pat. Nos. 4,001,140; 4,087,376; 4,089,802 and 4,100,103), Greene et al. (U.S. Pat. Nos. 2,800,458; 2,800,457 and 2,730,456), Hayford (U.S. Pat. No. 4,444,699), Hasler et al. (U.S. Pat. No. 5,105,823), Stevens (U.S. Pat. No. 4,197,346), Riecke (U.S. Pat. No. 4,622,267), Greiner et al. (U.S. Pat. No. 4,547,429), and Brown (U.S. Pat. No. 4,552,881), among others and as taught by Herbig in the chapter entitled "Microencapsulation" in Kirk-Othmer Encyclopedia of Chemical Technology, V. 16, pages 438-463.

FIELD OF THE INVENTION

This invention relates to capsule manufacturing, processes of making and microcapsules produced by such processes.

DESCRIPTION OF THE RELATED ART

Each patent described throughout this application is incorporated herein by reference to the extent each provides guidance regarding microencapsulation processes and materials.

Interfacial polymerization is a process wherein a microcapsule wall, typically a polyamide, an epoxy resin, a polyurethane, a polyurea or the like is formed at an interface between two phases. Riecke, U.S. Pat. No. 4,622,267 discloses an interfacial polymerization technique for preparation of microcapsules. The core material is initially dissolved in a solvent and an aliphatic diisocyanate soluble in the solvent mixture is added. Subsequently, a nonsolvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurethane shells. Jahns, U.S. Pat. No. 5,292,835 teaches polymerizing esters of acrylic acid or methacrylic acid with polyfunctional monomers. Specifically illustrated are reactions of polyvinylpyrrolidone with acrylates such as butanediol diacrylate or methyl methacrylate together with a free radical initiator.

Schwantes, U.S. Pat. Pub. 2009/0274905 teaches cationic microcapsule particles where the wall in the reaction product of an amine acrylate with a multifunctional methacrylate in the presence of an acid and initiator; or alternatively an acid acrylate and multifunctional (meth)acrylate in the presence of a base and initiator.

Microcapsules whose shell wall comprises on one surface a first (meth)acrylate polymer and on its other surface a second (meth)acrylate polymer are taught in Feng, et al., U.S. Pat. No. 9,714,397.

A need exists in the art for more robust microcapsules which retain capsule contents over time, until fractured or otherwise made available. Especially with (meth)acrylate capsules and such capsules with multi walls, a need exists for (meth)acrylate microcapsules that have a surface charge or hydrophilic functional groups. Such capsules would reduce or eliminate need for separate deposition aids where adherence to target surfaces is desirable and provide for a more custom-tailored release profile.

The microcapsules are useful in a variety of challenging environments, such as use with fabric enhancers, laundry, phase change and other industrial and commercial applications.

Definition

As used herein, reference to the term "(meth)acrylate" or "(meth)acrylic" is to be understood as referring to both the acrylate and the methacrylate versions of the specified monomer, oligomer and/or prepolymer, (for example "isobornyl(meth)acrylate" indicates that both isobornyl methacrylate and isobornyl acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible). Similarly, the use of the phrase "prepolymer" means that the referenced material may exist as a prepolymer or combination of oligomers and prepolymers. Similarly, it is to be understood that the general reference herein to (meth)acrylate or (meth)acrylates, e.g., "water soluble (meth)acrylates", "water phase (meth)acrylate", etc., is intended to cover or include the "(meth)acrylate monomers and/or oligomers." Additional, the descriptors "water soluble or dispersible", water soluble", and "water dispersible" when referencing certain (meth)acrylate monomers and/or oligomers or initiators means that the specified component is soluble or dispersible in the given matrix solution on its own or in the presence of a suitable solubilizer or emulsifier or upon attainment of certain temperatures and/or pH.

Each alkyl moiety herein, unless otherwise indicated, can be from $C_1$ to $C_8$, or even from $C_1$ to $C_{24}$. Poly(meth)acrylate materials are intended to encompass a broad spectrum of polymeric materials including, for example, polyester poly (meth)acrylates, urethane and polyurethane poly(meth)acrylates (especially those prepared by the reaction of a hydroxyalkyl(meth)acrylate with a polyisocyanate or a urethane polyisocyanate), methyl cyanoacrylate, ethyl cyanoacrylate, diethylene glycol di(meth)acrylate, trimethylolpropane tri (meth)acrylate, ethylene glycol di(meth)acrylate, allyl (meth)acrylate, glycidyl(meth)acrylate, (meth)acrylate functional silicones, di-, tri- and tetraethylene glycol di(meth) acrylate, dipropylene glycol di(meth)acrylate, polyethylene glycol di(meth)acrylate, di(pentamethylene glycol) di(meth) acrylate, ethylene di(meth)acrylate, neopentyl glycol di(meth)acrylate, trimethylolpropane tri(meth)acrylate, ethoxylated bisphenol A di(meth)acrylates, bisphenol A di(meth) acrylates, diglycerol di(meth)acrylate, tetraethylene glycol dichloroacrylate, 1,3-butanediol di(meth)acrylate, neopentyl di(meth)acrylate, trimethylolpropane tri(meth)acrylate, polyethylene glycol di(meth)acrylate and dipropylene glycol di(meth)acrylate and various multifunctional (meth)acrylates and multifunctional amine (meth)acrylates. Monofunctional acrylates, i.e., those containing only one acrylate group, may also be advantageously used. Typical monoacrylates include 2-ethylhexyl(meth)acrylate, 2-hydroxyethyl (meth)acrylate, cyanoethyl(meth)acrylate, 2-hydroxypropyl (meth)acrylate, p-dimethyl aminoethyl(meth)acrylate, lauryl (meth)acrylate, cyclohexyl(meth)acrylate, tetrahydrofurfuryl(meth)acrylate, chlorobenzyl(meth)acrylate, amino alkyl(meth)acrylate, various alkyl(meth)acrylates and glycidyl(meth)acrylate. Of course, mixtures of (meth)acrylates or their derivatives as well as combinations of one or more (meth)acrylate monomers, oligomers and/or prepolymers or their derivatives with other copolymerizable monomers, including acrylonitriles and methacrylonitriles may be used as well.

SUMMARY OF THE INVENTION

Figure 1:
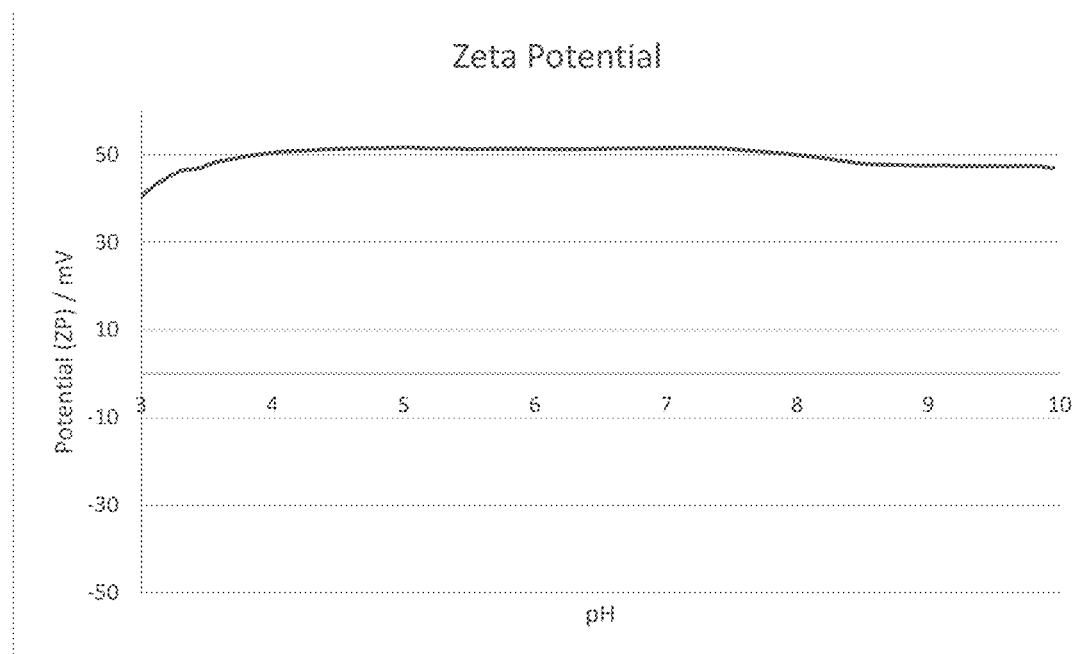
FIG. 1 is a graph of zeta potential of the microcapsules according to Example 2.

The invention describes a composition comprising a microcapsule comprising a core material and a shell that surrounds the core material, the core material comprising a benefit agent, the shell comprising a reaction product of at least one amphiphilic block prepolymer, the shell having an external surface having a cationic or anionic charge, and the external surface having hydrophilic functional groups. The microcapsule is made by a process comprising a series of steps. The process comprises pre-reacting one or more water phase monomers, at least one having a hydrophilicity index of at least 30, or even at least 35, to form an amphiphilic block polymer by the steps comprising a) dissolving or dispersing one or more free radical initiators in a first water phase to provide a source of free radicals upon activation, b) dissolving or dispersing in a second water phase, one or more water soluble (meth)acrylate monomer or monomers having hydrophilic functional groups, such as hydrophilic functional groups selected from one or more of the groups consisting of carboxy, amine, sulfonic and quaternary ammonium groups, c) combining the first water phase with the second water phase and activating the initiator to form free radicals of the initiator and to pre-react the monomers forming a first prepolymer, the first prepolymer having active free radical end groups, d) dispersing in a third water phase, a water insoluble but water dispersible multifunctional(meth)acrylate monomer having hydrophobic segments, and optionally an additional water soluble (meth)acrylate monomer, e) combining the first prepolymer with the multifunctional monomer of the third water phase and f) heating, or otherwise activating or reacting such as with actinic radiation, the combined first prepolymer and the multifunctional monomer, thereby forming a polymer by free radical polymerization of the first prepolymer and the multifunctional monomer, the resulting polymer being a block polymer, the block polymer having end groups comprising a free radical. The free radical groups of the block polymer promote chain growth of the block polymer increasing the molecular weight of the block polymer during the heating step, said block prepolymer being amphiphilic with hydrophobic segments and hydrophilic functional groups. The block polymer's hydrophobic segments and increasing molecular weight decrease solubility of the block polymer. This results in precipitating the block polymer and/or provides a means of moving or biasing the block polymer out from the water phase and/or toward an interface, The second step is pre-reacting one or more oil phase monomers at least one having a hydrophilicity index of 20 or less, or even 15 or less, to form an amphiphilic prepolymer by steps comprising a) providing an oil phase comprising optionally an initiator and a benefit agent core material, and at least one oil soluble multifunctional (meth)acrylate monomer and wherein from 0 to 100% by weight of the oil phase monomers comprise an oil soluble or dispersible hydrophilic (meth)acrylate monomer having hydrophilic functional groups such as a hydrophilic functional group selected from one or more of the groups consisting of carboxy, amine, sulfonic acid and quaternary ammonium functional groups and b) heating to pre-react the monomers of the oil phase forming an oil phase prepolymer which is amphiphilic.

In a third step an emulsion is formed by steps comprising, a) emulsifying the oil phase into the water phase using high shear agitation to form an emulsion of droplets of the oil phase of less than 100 microns dispersed in the water phase and b) further reacting the emulsion of the oil phase and water phase by heating the emulsion for a time and temperature, or by actinic irradiation, sufficient to form a microcapsule shell at interfaces of the oil droplets and water of the emulsion, said microcapsule shell surrounding the benefit agent core material and said microcapsule shell having a surface charge and having hydrophilic functional groups.

The resulting microcapsules have a zeta potential, measured at a pH of 7, of from +70 to −70.

Desirably, for safety, the various heating steps to activate the initiators and for polymerization are carried out under an inert or nitrogen blanket. The inert blanket displaces oxygen and minimizes side reactions. Inert, for purpose hereof, means gases which minimize flammability and can include nitrogen, $CO_2$, argon, or any of the other noble gases.

The present teachings pertain to the production of the novel microcapsules and methods of forming the same, which exhibit improved release or retention characteristics combined with excellent physical properties and attributes. Capsules according to the invention have surface charge or hydrophilic functional groups. Capsules according to the invention have improved charge or adherence to target surfaces and can reduce or even eliminate the amount of deposition aids needed.

In another aspect, the oil phase can include, in addition, one or more additives consisting of an initiator and/or a water soluble dispersible emulsifier.

Advantageously, the hydrophilic functional groups on the surface of the microcapsule shell are polar. The amphiphilic block prepolymer of the combined water phases can also be functional as an emulsifier, and in the combined water phases, the block prepolymer terminal groups are functional as an initiator. In forming the microcapsule shell, the block prepolymer hydrophilic segments provide a driving force to bias movement of the prepolymer toward the oil-water interface of the emulsion droplets of the oil phase in the water phase.

The microcapsules can be used as a slurry of microcapsules, in coatings, as an additive to other materials, incorporated in or on fibers or textiles, or incorporated in or on polymeric materials, foams or other substrates. Optionally after microcapsule formation, the formed microcapsule can be isolated from the water phase or continuous phase, such as by decanting, dewatering, centrifuging, spray-drying, evaporation, freeze drying or other solvent removal or drying process.

DETAILED DESCRIPTION

The present invention discloses a composition and process of forming a population of microcapsules. The microcapsules comprise an oil soluble or dispersible benefit agent core material and a shell surrounding the benefit agent core material. The shell comprises the reaction product of at least one amphiphilic block living prepolymer.

Specifically, in the invention, there are provided microcapsules comprising a core material of a benefit agent and a shell that surrounds the core material. The shell has an external surface having cationic or anionic charge, and the shell has hydrophilic functional groups such as carboxy, amine, sulfonic or quaternary ammonium groups.

The shell comprises the reaction product of an amphiphilic block living prepolymer formed in the water phase with a dissolved or dispersed multifunctional (meth)acrylate monomer of the oil phase. The reaction, once a prepolymer forms in the respective water and oil phases, is interfacial. The oil is dispersed in the water phase forming droplets of the oil phase in the water phase.

In the invention a living (meth)acrylate prepolymer is used to functionalize the surface of the forming shell of the microcapsule. The living prepolymer can even serve as an emulsifier itself and create a tendency for the prepolymer to concentrate on the interface and thereby stabilize the oil-water emulsion. The living prepolymer initiates polymerization from the water side of the interface, and even allows cationic groups to attach to the shell surface permanently by chemical reaction.

The main purpose of the living acrylate prepolymer in the present microencapsulation system is to functionalize the shell surface. The living polymers consist partially of cationic groups (such as quaternary ammonium), which can serve as an emulsifier and therefore have the tendency to concentrate on the water-oil interface and stabilize the emulsion. The prepolymer initiates the polymerization from the waterside of the interface. It allows the cationic groups to attach to the surface permanently by chemical reaction. The capsules formed from living prepolymers according to the invention show strong positive charge. Due to the pH-independence of, for example, quaternary ammonium groups, the microcapsules can even keep consistent strong positive charge over a wide range of pH values.

Amphiphilic block copolymers of the invention contain chemically connected segments of hydrophilic and hydrophobic groups. The resulting block polymers can be of the AB type, ABA type or ABC triblock copolymers, including terpolymers.

Amphiphilic block copolymers can be tailored to have a tendency, via a predominance of hydrophobic segments, to tend to drive the forming copolymer out of the water phase toward the interface of the water and oil phase.

Such prepolymers have a tendency to form micelle-type structures by assembling at the water-oil interface and surrounding dispersed oil droplets in the water phase.

Block copolymers have the additional benefit of bringing together characteristics of a variety of polymer segments. The segments of the block prepolymer forming the block polymer can impart characteristics such as stability or can impart attributes of polar groups.

The capsules according to the invention are useful with a wide variety of capsule contents ("core materials" or "benefit agents") including, by way of illustration and without limitation, internal phase oils, solvent oils, phase change materials, lubricants, dyes, perfumes, fragrances, cleaning oils, polishing oils, flavorants, nutrients, sweeteners, chromogens, pharmaceuticals, fertilizers, herbicides, biological actives, scents, and the like. The microcapsule core materials can include materials which alter rheology or flow characteristics or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. The core material typically should be dispersible or sufficiently soluble in the capsule internal phase material namely in the internal phase oil or soluble or dispersible in the monomers or oligomers solubilized or dispersed in the internal phase oil. The core materials are preferably liquid but can be solid depending on the materials selected, and with temperatures appropriately adjusted to effect dispersion.

Useful benefit agents or core materials include perfume raw materials, such as alcohols, ketones, aldehydes, esters, ethers, nitriles, alkenes, fragrances, fragrance solubilizers, essential oils, phase change materials, lubricants, colorants, cooling agents, preservatives, antimicrobial or antifungal actives, herbicides, antiviral actives, antiseptic actives, antioxidants, biological actives, deodorants, emollients, humectants, exfoliants, ultraviolet absorbing agents, self-healing compositions, corrosion inhibitors, sunscreens, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof. Phase change materials useful as core materials can include, by way of illustration and not limitation, paraffinic hydrocarbons having 13 to 28 carbon atoms, various hydrocarbons such n-octacosane, n-heptacosane, n-hexacosane, n-pentacosane, n-tetracosane, n-tricosane, n-docosane, n-heneicosane, n-eicosane, n-nonadecane, octadecane, n-heptadecane, n-hexadecane, n-pentadecane, n-tetradecane, n-tridecane. Phase change materials can alternatively, optionally in addition include crystalline materials such as 2,2-dimethyl-1,3-propanediol, 2-hydroxymethyl-2-methyl-1,3-propanediol, acids of straight or branched chain hydrocarbons such as eicosanoic acid and esters such as methyl palmitate, fatty alcohols and mixtures thereof.

The invention makes possible tailored surface charge of (meth)acrylate-based microcapsules by chemical attachment on the surface, especially the external surface of the microcapsule, through the charged domains or charged pendant groups of the resulting polymer.

The surface charge can improve the deposition of the microcapsules on substrates such as textiles, skin, hair, fibers, or other surfaces.

Surface charge can also be advantageously employed to improve adhesion of microcapsules on surfaces such as foam or bedding material.

Surface charge can also be advantageously adapted to create agglomerates to facilitate ease of filtration where a high solids, cake, or dry powder of microcapsules is desirable.

If desired the microcapsules can be separated from the aqueous medium. The slurry can either be used as is, used as a dewatered cake, or used in dry powder form depending on the application.

The process of the invention is based on formation of an oil-in-water emulsion to effect encapsulation. In the process of the invention the combined first and second water phases are heated to prereact the monomers forming a first prepolymer. The first prepolymer has the hydrophilic functional groups.

The first prepolymer of the combined first and second water phases is dispersed into a third water phase. The third water phase includes a water insoluble but water dispersible multifunctional (meth)acrylate monomer, and optionally an additional water soluble (meth)acrylate monomer.

Significantly, the invention provides microcapsules wherein the shell is fashioned from prepolymers formed in situ in one or more water phases and in one or more oil phases. Droplets of oil are emulsified into the water, and shell is formed at interfaces of the oil and water, with the shell surrounding the oil droplets.

The wall shell comprises one surface forming from a first (meth)acrylate composition derived from the water phase, and the surface of the shell also being derived from the oil phase. The shell is the reaction product of at least one amphiphilic (meth)acrylate block living polymer with the shell having an external surface having a cationic or anionic charge. The external surface alternatively, but preferably, may have hydrophilic functional groups.

In forming the core shell microcapsule, a first water phase is provided. Dissolved or dispersed in the first water phase are one or more free radical initiators. The initiators are preferably thermally activated and upon activation, whether by heat, light or other energy means to activate, provide a source of free radicals.

A second water phase is provided. In the second water phase, one or more water soluble (meth)acrylate monomers are dissolved or dispersed. The water soluble (meth)acrylate monomer is selected to have hydrophilic functional groups. Examples of such hydrophilic functional groups can include hydroxy, phosphate, carboxy, amine, sulfonic or quaternary ammonium groups.

The first and second water phases are combined, and the initiator is activated, forming free radicals which prereact the monomer forming a first prepolymer.

A third water phase is provided, into which is dispersed a water insoluble but water dispersible multifunctional (meth) acrylate monomer. In addition to the water dispersible multifunctional (meth)acrylate monomer, an additional water-soluble mono-, di- or poly-functional (meth)acrylate monomer can be included in the third water phase. The order of addition for combining of monomers of the water phase can be varied.

The water phase monomers can also include one or more free-radically polymerizable unsaturated monomers such as ethylenically unsaturated monomers particularly di- or polyfunctional monomers.

Additional optional water phase monomers can be selected from comprises one or more water soluble or dispersible (meth)acrylate monomers and/or oligomers/prepolymers. Those skilled in the art will recognize and appreciate that certain useful water phase monomers will be water soluble or water dispersible, particularly in the presence of a suitable emulsifier and or solubilizer and/or at elevated temperature and/or adjusted pH and may be used as or as a portion of the water phase monomer. Monomers may be amphiphilic, having constituents or groups that make them both hydrophilic and hydrophobic: the degree of hydrophilicity and/or hydrophobicity (or even lipophilicity) will be determinative of the extent of their use in one phase or the other. For the respective water and oil phases the hydrophilicity index described herein guides selection of the useful multifunctional monomers.

The water phase monomers generally comprise 1 to 100 wt %, preferably 30 to 100 wt %, of at least one free radical polymerizable multifunctional monomer having a hydrophilicity index of at least 30; 0 to 99 wt %, preferably, 0.01 to 90 wt %, or even from 10 to 90 wt % of at least one (meth)acrylate monomer having hydroxy, phosphate, carboxy, amine, sulfonic and/or quaternary ammonium groups, and 0 to 60 wt %, preferably 0 to 30 wt %, of other poly or mono-functional monomers. Preferably the monomers are difunctional monomers or comprise a predominant amount, i.e., 50 mole % or more, of a difunctional monomer.

Exemplary water phase monomers can be selected from ethylenically amine modified polyether (meth)acrylate oligomers, hexafunctional aromatic urethane (meth)acrylate oligomers, hydroxyethyl(meth)acrylate, hydroxypropyl (meth)acrylate, methyl methacrylate, butanediol di(meth) acrylate, hexanediol di(meth)acrylate, ethoxylated bisphenol-A diacrylate, ethoxylated bisphenol-A dimethacrylate, isobornyl (meth)acrylate, pentaerythritol tri(meth)acrylate, pentaerythritol tetra(meth)acrylate, penta(meth)acrylate ester, diethylene glycol di(meth)acrylate, dipropylene glycol di(meth)acrylate, triethylene glycol di(meth)acrylate, tripropylene glycol di(meth)acrylate, neopentyl glycol di(meth) acrylate, trimethylol propane tri(meth)acrylate, methoxy polyethylene glycol mono(meth)acrylate, ethoxylated trimethylolpropane tri(meth)acrylate, and ethoxylated pentaerythritol tetra(meth)acrylate, difunctional aliphatic epoxy (meth)acrylates, polyethylene glycol di(meth)acrylate, polypropylene glycol di(meth)acrylate, alkoxylated mono- or multi-functional (meth)acrylate ester, polyester (meth) acrylate oligomers, amine modified polyether (meth)acrylate oligomers and the like.

Other monomers, especially polyfunctional monomers can be included that will co-polymerize with the water phase monomers are known to those skilled in the art and widely used in free-radical encapsulation processes.

The amount of water phase monomer employed in the water phase composition is dependent, at least in part, on the amount of core phase monomer present in the core phase composition. Generally speaking, the ratio by weight of the water phase monomer to the oil or core phase monomer is preferably in the range of from about 1:3 to about 1:50 or more, preferably from about 1:6 to 1:50. Generally, such weight ratios will relate to the presence of less than 20 wt %, preferably less than 10 wt % of the water phase monomer based on the respective water phase composition. It is to be appreciated that sufficient monomer must be present to form a satisfactory wall in a reasonable time frame. The concentration of the respective water phase monomer is at least 0.5 wt %, or even 1 wt % or even at least 5 wt %, or even at least 15 wt % or even 20 wt %. Nevertheless, it is also to be noted that lower, though acceptable, concentrations of water phase monomer are desired as higher concentrations, especially those near or in excess of 20 wt %, have an increased risk of forming a gel.

Another factor that is controlling the amount of water phase monomer incorporated in each respective water phase composition is the amount of core phase composition intended to be present in the emulsion and the desired thickness of the shell wall. In this regard, the weight ratio of oil phase composition to total water phase monomers is from about 10:90 to 98:2, respectively. An especially preferred microcapsule will have from 70 to 90% core and 30-10% shell, more preferably from 75 to 85% core, with a useful microcapsule comprising about 82% core and about 18% shell by weight.

The multifunctional (meth)acrylate monomer of the respective water phase is screened to have an appropriate hydrophilicity index of at least 30, or even at least 25, calculated as provided herein. Examples of calculated hydrophilicity index values (HPI) are listed in Table 1. Similarly, HPI values are readily able to be determined for the various monomers mentioned in this specification by the equation taught herein, Similarly, a multifunctional (meth)acrylate monomer of the oil phase is screened to have a hydrophilicity index of 20 or less, or even of 25 or less.

The multifunctional monomer is selected to be water dispersible and selected from materials such as ethoxylated trimethylolpropane triacrylate, or polyethylene glycol diacrylate, or polyethylene glycol dimethacrylate.

Illustrations of multifunctional (meth)acrylate or methacrylate monomers or oligomers also include by way of illustration and not limitation, allyl methacrylate; triethylene glycol dimethacrylate; ethylene glycol dimethacrylate, diethylene glycol dimethacrylate, aliphatic or aromatic urethane diacrylates, difunctional urethane acrylates, ethoxylated aliphatic difunctional urethane methacrylates, aliphatic or aromatic urethane dimethacrylates, epoxy acrylates, epoxymethacrylates; tetraethylene glycol dimethacrylate; polyethylene glycol dimethacrylate; 1,3 butylene glycol diacrylate; 1,4-butanediol dimethacrylate; 1,4-butaneidiol diacrylate; diethylene glycol diacrylate; 1,6 hexanediol diacrylate; 1,6 hexanediol dimethacrylate; neopentyl glycol diacrylate; polyethylene glycol diacrylate; tetraethylene glycol diacrylate; triethylene glycol diacrylate; 1,3 butylene glycol dimethacrylate; tripropylene glycol diacrylate; ethoxylated bisphenol diacrylate; ethoxylated bisphenol dimethyl acrylate; dipropylene glycol diacrylate; alkoxylated hexanediol diacrylate; alkoxylated cyclohexane dimethanol diacrylate; propoxylated neopentyl glycol diacrylate, trimethylolpropane trimethacrylate; trimethylolpropane triacrylate, pentaerythritol triacrylate, ethoxylated trimethylolpropane triacrylate, propoxylated trimethylolpropane triacrylate, propoxylated glyceryl triacrylate, ditrimethylolpropane tetraacrylate, dipentaerythritol pentaacrylate, ethoxylated pentaerythritol tetraacrylate.

The hydrophilicity index of the foregoing multifunctional monomers is readily determinable based from the HPI formula set forth in this specification. Using the hydrophilicity index, as appropriate multifunctional (meth)acrylate is selectable for each of the respective water and oil phases.

The optional additional water soluble (meth)acrylate of the third water phase is selected from monomers which are soluble or dispersible in water, generally having a solubility greater than 3 g/ml and at least one ethylenically unsaturated polymerizable group.

The oil phase comprises an optional initiator, a benefit agent core material and at least one oil soluble multifunctional (meth)acrylate monomer. In addition, the oil phase can also comprise from 0 to 100% by weight of the oil phase monomers of an oil soluble or dispersible hydrophilic (meth) acrylate monomer having hydrophilic functional groups selected form the group consisting of carboxy, amine, sulfonic and quaternary ammonium groups.

In the oil phase at least one oil soluble multifunctional (meth)acrylate monomer can contain two or more double bonds, preferably two or more acrylate or methacrylate functional groups. Multifunctional monomers and oligomers include, by way of illustration and not limitation, allyl methacrylate; triethylene glycol dimethacrylate; ethylene glycol dimethacrylate; diethylene glycol dimethacrylate; aliphatic or aromatic urethane acrylates, such as hexa-functional aromatic urethane acrylates; ethoxylated aliphatic difunctional urethane methacrylates; aliphatic or aromatic urethane methacrylates, such as tetra-functional aromatic methacrylates; epoxy acrylates; epoxymethacrylates; tetraethylene glycol dimethacrylate; polyethylene glycol dimethacrylate; 1,3 butanediol diacrylate; 1,4-butanediol dimethacrylate; 1,4-butanediol diacrylate; diethylene glycol diacrylate; 1,6 hexanediol diacrylate; 1,6 hexanediol dimethacrylate; neopentyl glycol diacrylate; polyethylene glycol diacrylate; tetraethylene glycol diacrylate; triethylene glycol diacrylate; 1,3 butylene glycol dimethacrylate; tripropylene glycol diacrylate; ethoxylated bisphenol A diacrylate; ethoxylated bisphenol A dimethyl acrylate; dipropylene glycol diacrylate; alkoxylated hexanediol diacrylate; alkoxylated cyclohexane dimethanol diacrylate; propoxylated neopentyl glycol diacrylate; trimethylolpropane trimethacrylate; trimethylolpropane triacrylate; pentaerythritol triacrylate; pentaerythritol tetramethacrylate; ethoxylated trimethylolpropane triacrylate; propoxylated trimethylolpropane triacrylate; propoxylated glyceryl triacrylate; ditrimethylolpropane tetraacrylate; dipentaerythritol pentaacrylate; ethoxylated pentaerythritol tetraacrylate; bis-phenol A diacrylate; bis-phenol A dimethacrylate, hexafunctional aromatic urethane acrylate; hexa-functional aromatic urethane methacrylate; and the like.

The oil phase oil soluble or dispersible hydrophilic (meth) acrylate monomers can be selected from hydroxy(meth) acrylate, (meth)acrylate phosphate, carboxy(meth)acrylate, quaternary ammonium (meth)acrylate, or ammonium (meth) acrylate, amino alkyl(meth)acrylate, or dialkyl amino alkyl (meth)acrylate. Such materials, by way of illustration and not limitation include tertiary butyl amino ethyl acrylate, diethylamine ethyl methacrylate, dimethyl amino ethyl methacrylate, 4-hydrozino benzene sulfonic acid (meth) acrylic acid, amine modified alkoxylated trialkanol alkyl triacrylate, such as amine modified ethoxylated trimethylol propane triacrylate, diacrylate amine, triacrylate amine, amine modified polyether acrylate and amine modified polyether methacrylate. The hydrophilic (meth)acrylate monomers of the oil phase comprise from about 0.015 to about 10% by weight of the oil phase monomers, or even from about 1% to about 10% of the oil phase monomers forming the polymer shell of the microcapsule.

In the invention, the multifunctional monomers for the respective water and oil phases are selected based on their hydrophilicity index (HPI). Hydrophilicity index is defined as the weight percentage of oxygen and nitrogen in the non-acrylate of non-methacrylate portion of the monomer molecule.

$$HPI = \frac{\text{weight of oxygen} + \text{weight of nitrogen}}{\text{total weight of monomer}} \times 100$$

In the calculation, the oxygen and nitrogen in the acrylate moiety or methacrylate moiety is included in the denominator but omitted from the numerator. The HPI index correlates to a relative increase or decrease in water or oil solubility contributed by parts of the molecule other than the acrylate or methacrylate moiety.

Table 1 provides an illustrative list of the hydrophilicity index of various monomers.

TABLE 1

| Material | Name | C | H | O | N | Acrylates | Methacrylate | MW | Ac MW | MW-Ac | MAc MW | O-Ac | H-Ac | C-Ac | HPI |
|---|---|---|---|---|---|---|---|---|---|---|---|---|---|---|---|
| SR415 | ethoxylated (20) trimethylolpropane triacrylate | 55 | 100 | 26 | 0 | 3 | 0 | 1176 | 213 | 963 | 0 | 20 | 88 | 46 | 33.23 |
| SR206 | ethylene glycol dimethacrylate | 10 | 14 | 4 | 0 | 0 | 2 | 198 | 0 | 28 | 170 | 0 | 2 | 2 | 0.00 |
| SR502 | ethoxylated (9) trimethylolpropane triacrylate | 33 | 56 | 15 | 0 | 3 | 0 | 692 | 213 | 479 | 0 | 9 | 44 | 24 | 30.06 |
| SR210 | polyethylene (200) glycol dimethacrylate | 16 | 26 | 8 | 0 | 0 | 2 | 346 | 0 | 176 | 170 | 4 | 14 | 8 | 36.36 |
| SR259 | polyethylene glycol (200) diacrylate | 14 | 22 | 8 | 0 | 2 | 0 | 318 | 142 | 176 | 0 | 4 | 14 | 8 | 36.36 |
| SR344 | polyethylene glycol (400) diacrylate | 24 | 42 | 13 | 0 | 2 | 0 | 538 | 142 | 396 | 0 | 9 | 34 | 18 | 36.36 |
| SR610 | polyethylene glycol (600) diacrylate | 32 | 58 | 17 | 0 | 2 | 0 | 714 | 142 | 572 | 0 | 13 | 50 | 26 | 36.36 |
| SR368 | tris (2-hydroxy ethyl) isocyanurate triacrylate | 18 | 21 | 9 | 3 | 3 | 0 | 423 | 213 | 210 | 0 | 3 | 9 | 9 | 42.86 |
| SR351 | trimethylolpropane triacrylate | 15 | 20 | 6 | 0 | 3 | 0 | 296 | 213 | 83 | 0 | 0 | 8 | 6 | 0.00 |
| SR350 | trimethylolpropane trimethacrylate | 18 | 26 | 6 | 0 | 0 | 3 | 338 | 0 | 83 | 255 | 0 | 8 | 6 | 0.00 |
| SR444 | pentaerythritol triacrylate | 14 | 18 | 7 | 0 | 3 | 0 | 298 | 213 | 85 | 0 | 1 | 6 | 5 | 18.82 |
| SR295 | pentaerythritol tetraacrylate | 17 | 20 | 8 | 0 | 4 | 0 | 352 | 284 | 68 | 0 | 0 | 4 | 5 | 0.00 |
| SR355 | di-trimethylolpropane tetraacrylate | 24 | 34 | 9 | 0 | 4 | 0 | 466 | 284 | 182 | 0 | 1 | 18 | 12 | 8.79 |
| SR399 | dipentaerythritol pentaacrylate | 28 | 34 | 13 | 0 | 6 | 0 | 578 | 426 | 152 | 0 | 1 | 10 | 10 | 10.53 |
| SR454 | ethoxylated (3) trimethylolpropane triacrylate | 21 | 32 | 9 | 0 | 3 | 0 | 428 | 213 | 215 | 0 | 3 | 20 | 12 | 22.33 |
| SR494 | ethoxylated (4) pentaerythritol tetraacrylate | 23 | 36 | 10 | 0 | 3 | 0 | 472 | 213 | 259 | 0 | 4 | 24 | 14 | 24.71 |
| SR499 | ethoxylated (6) trimethylolpropane triacrylate | 27 | 44 | 12 | 0 | 3 | 0 | 560 | 213 | 347 | 0 | 6 | 32 | 18 | 27.67 |
| SR348 | ethoxylated (2) bisphenol A dimethacrylate | 27 | 32 | 6 | 0 | 0 | 2 | 452 | 0 | 282 | 170 | 2 | 20 | 19 | 11.35 |
| SR349 | ethoxylated (3) bisphenol A diacrylate | 27 | 32 | 7 | 0 | 2 | 0 | 468 | 142 | 326 | 0 | 3 | 24 | 21 | 14.72 |
| SR480 | ethoxylated (10) bisphenol A dimethacrylate | 43 | 64 | 14 | 0 | 0 | 2 | 804 | 0 | 634 | 170 | 10 | 52 | 35 | 25.24 |
| SR602 | ethoxylated (10) bisphenol A diacrylate | 41 | 60 | 14 | 0 | 2 | 0 | 776 | 142 | 634 | 0 | 10 | 52 | 35 | 25.24 |
| SR601 | ethoxylated (4) bisphenol A diacrylate | 29 | 36 | 8 | 0 | 2 | 0 | 512 | 142 | 370 | 0 | 4 | 28 | 23 | 17.30 |
| SR540 | ethoxylated (4) bisphenol A dimethacrylate | 31 | 40 | 8 | 0 | 0 | 2 | 540 | 0 | 370 | 170 | 4 | 28 | 23 | 17.30 |
| SR9035 | ethoxylated (15) trimethylolpropane triacrylate | 45 | 80 | 21 | 0 | 3 | 0 | 956 | 213 | 743 | 0 | 15 | 68 | 36 | 32.30 |
| SR508 | dipropylene glycol diacrylate | 12 | 18 | 5 | 0 | 2 | 0 | 242 | 142 | 100 | 0 | 1 | 10 | 6 | 16.00 |
| SR9038 | ethoxylated (30) BPA diacrylate | 81 | 140 | 34 | 0 | 2 | 0 | 1656 | 142 | 1514 | 0 | 30 | 132 | 75 | 31.70 |

Provided the applicable hydrophilicity index parameter is met, the hydrophobic segments of the multifunctional (meth)acrylate monomer desirably are of the type such as with aliphatic segments or groups. Water insoluble vinyl groups such as of 8 to 30 carbons or long chain aliphatic groups of 6 to 40 carbons can be useful. Water insoluble vinyl groups can include acrylamide segments, methacrylamide, vinyl methyl ether, vinyl pyrrolidone, N-vinyl oxazolidone, long chain acrylate esters, e.g. lauryl methacrylate, stearyl methacrylate type segments or groups. The multifunctional monomer of the water phase can be anywhere from 0.5 to 90 wt %, preferably 0.5 to 50 wt %, or even 0.5 to 30 wt % of the shell. The multifunctional monomer of the oil phase similarly can be 0.5 to 90 wt %, but preferably 0.5 to 30 wt %, or even 0.5 to 10 wt % of the shell.

The initiators are energy activated meaning generating free radicals when subjected to heat or other energy input such as actinic radiation or ion beam. Preferred initiators include peroxy initiators, azo initiators, peroxides, and compounds such as 2,2'-azobismethylbutyronitrile, dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis (isobutylnitrile), 2,2'-azobis(2,4-dimethylpentanenitrile), 2,2'-azobis(2,4-dimethylvaleronitrile), 2,2'-azobis(2-methylpropanenitrile), 2,2'-azobis(methylbutyronitrile), 1,1'-azobis(cyclohexanecarbonitrile), 1,1'-azobis(cyanocyclohexane), benzoyl peroxide, decanoyl peroxide; lauroyl peroxide; benzoyl peroxide, di(n-propyl) peroxydicarbonate, di(sec-butyl) peroxydicarbonate, di(2-ethylhexyl) peroxydicarbonate, 1,1-dimethyl-3-hydroxybutyl peroxyneodecanoate, .alpha.-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoyl peroxy)hexane, t-amyl peroxy-2-ethylhexanoate, t-butyl peroxy-2-ethylhexanoate, t-butyl peroxyacetate, di-t-amyl peroxyacetate, t-butyl peroxide, di-t-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like. Blends of initiators can also be employed. Initiators are available commercially, such as Vazo initiators, which typically indicate a decomposition temperature for the initiator. Preferably the initiator is selected to have a decomposition point of about 50° C. or higher. Usefully multiple initiators are employed, either as a blend in the oil phase, or in either of the oil or water phases. Preferably initiators are selected to stagger the decomposition temperatures at the various steps, pre-polymerization, wall formation and hardening or polymerizing of the capsule wall material. For example, a first initiator in the oil phase can decompose at 55° C., to promote prepolymer formation, a second can decompose at 60° C. to aid forming the wall material. Optionally a third initiator can decompose at 65° C. to facilitate polymerization of the capsule wall material. The total amount of initiator can be typically as low as 0.1 weight percent or as high as 10 weight percent.

The terms dispersed phase or oil phase are used interchangeably for purposes hereof and can be selected from hydrocarbons, more particularly hydrocarbon solvents and the solvents can include by way of illustration and not limitation, ethyl diphenylmethane, butyl biphenyl ethane, benzyl xylene, alkyl biphenyls such as propyl biphenyl and butyl biphenyl, dialkyl phthalates e.g. dibutyl phthalate, dioctyl phthalate, dinonyl phthalate and ditridecylphthalate; 2,2,4-trimethyl-1,3-pentanediol diisobutyrate, alkyl benzenes such as dodecyl benzene; but also carboxylates, ethers, or ketones such as diaryl ethers, di(aralkyl)ethers and aryl aralkyl ethers, ethers such as diphenyl ether, dibenzyl ether and phenyl benzyl ether, liquid higher alkyl ketones (having at least 9 carbon atoms), alkyl or aralky benzoates, e.g., benzyl benzoate, alkylated naphthalenes such as dipropylnaphthalene, partially hydrogenated terphenyls; high-boiling straight or branched chain hydrocarbons, arenes and alkaryl hydrocarbons such as toluene, vegetable oils such as canola oil, soybean oil, coin oil, sunflower oil, or cottonseed oil, methyl esters of fatty acids derived from transesterification of canola oil, soybean oil, cottonseed oil, corn oil, sunflower oil, pine oil, lemon oil, olive oil, or methyl ester of oleic acid, vegetable oils, esters of vegetable oils, e.g. soybean methyl ester, straight chain saturated paraffinic aliphatic hydrocarbons of from 10 to 13 carbons; $C_8$-$C_{42}$ esters, ethyl hexanoate, methyl heptanoate, butyl butyrate, methyl benzoate, methyl such as nonoate, methyl decanoate, methyl dodecanoate, methyl octanoate, methyl laurate, methyl myristate, methyl palm itate, methyl stearate, ethyl heptanoate, ethyl octanoate, ethyl nonoate, ethyl decanoate, ethyl dodecanoate, ethyl laurate, ethyl myristate, ethyl palmitate, ethyl stearate, isopropyl myristate, isopropyl palmitate, ethylhexyl palmitate, isoamyl laurate, butyl laurate, octyl octanoate, decyl decanoate, butyl stearate, lauryl laurate, stearyl palm itate, stearyl stearate, stearyl behenate, and behenyl behenate. Mixtures of the above can also be employed. Common diluents such as straight chain hydrocarbons can also be blended with the solvents, or blend of solvents. The solvent is selected on the basis of hydrophobicity and ability to disperse or solvate the core material and oil phase monomers.

In the process and composition of the invention, charge can be tailored to a high zeta potential at pH of 7, to a zeta potential in the range of from +70 to −70, and advantageously in many applications a range of from +40 to −65 is useful. Preferred is a zeta potential of greater than +70, or greater than +40, or greater than −70, or even greater than −40. Useful is a zeta potential of from +70 to +20, or from −20 to −70; or even a zeta potential of from +70 to +40, or from −40 to −70; or even from +70 to +50, or even from −50 to −70. "Greater than" or "higher than" in this context means a higher charge value, whether positive of negative. A more positive (greater positive value) or more negative charge value (greater negative value) is preferred.

Optionally, deposition aids can be included to increase deposition or adhesion of the microcapsules to various surfaces such as various substrates including but not limited to paper, fabric skin, hair, towels, or other surfaces. Deposition aids can include poly(acrylamide-co-diallyldimethylammonium chloride, poly (diallyldimethylammonium chloride, polyethylenimine, cationic polyamine, poly[(3-methyl-1-vinylimidazolium chloride)-co-(1-vinylpyrrolidone)], copolymer of acrylic acid and diallyldimethylammonium chloride, cationic guar, guar gum, an organopolysiloxane such as described in US Publication 20150030557, incorporated herein by reference. In a further embodiment, the above-described microcapsules can comprise a deposition aid, and in a further aspect the deposition aid coats the outer surface of the shell of the microcapsule.

In a further aspect the deposition aid can comprise a material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethyl aminoethyl methacrylate, polyvinyl amines, polyvinyl formamides, polyallyl amines and copolymers of polyvinyl amines, polyvinyl formam ides, and polyallyl amines and mixtures thereof.

In a yet further aspect, the deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, polyvinylpyrrolidone/vinyl acetate, polyvinyl pyrrolidone/dimethyl am inoethyl methacrylate, polyvinyl amines, polyvinyl formamides, polyallyl amines and copolymers of polyvinyl amines, polyvinyl formam ides, and polyallyl amines and mixtures thereof.

In the following examples, the abbreviations correspond to the following materials:

TABLE 2

| | Company/City | |
| --- | --- | --- |
| V50 | Wako Specialty Chemicals, Richmond, VA | 2,2'-azobis(2-methylpropionamidine) dihydrochloride |
| V501 | Wako Specialty Chemicals, Richmond, VA | 4,4'-azobis(4-cyanovaleric acid) |
| VAZO 67 | Chemours Company FC | 2,2'-azodi(2-methylbutyronitrile) |
| VAZO 88 | DuPont Chemical Solutions Enterprise | 1,1'-azobis(cyanocyclohexane) |
| SR415 | Sartomer, Arkema Group, Exton, PA | ethoxylated trimethylolpropane triacrylate |
| CD9055 | Sartomer, Arkema Group, Exton, PA | carboxylic acid monofunctional acrylate monomer |
| SR206 | Sartomer, Arkema Group, Exton, PA | ethylene glycol dimethacrylate |
| SR368 | Sartomer, Arkema Group, Exton, PA | tris (2-hydroxy ethyl) isocyanurate triacrylate |
| CN975 | Sartomer, Arkema Group, Exton, PA | hexafunctional urethane acrylate |
| TBAEMA | Sigma Aldrich, St. Louis, MO | 2-(tert-butylamino) ethyl methacrylate |
| TMACEMA | Sigma Aldrich, St. Louis, MO | 2-(methacryloxyethyl)trimethyl ammonium chloride |

Example 1

Polymer Preparation Process: Water phase 1, containing water and water phase initiator (V50), is placed in a jacketed steel reactor at 40° C. with mixing at 1000 rpm with a 4-tip flat mill, and a nitrogen blanket. The batch is heated from 40 to 75° C. and held at 75° C. for 45 minutes. A second water phase, containing a cationic hydrophilic acrylate monomer, such as [2-(methacryloyloxy)ethyl]trimethylammonium chloride (TMACEMA), (representing hydrophilic "block" of the polymer), is added, and the combined water phases held at 75° C. for 30 minutes. A third water phase, containing a mixture of a hydrophilic acrylate monomer, TMACEMA, and a hydrophobic, but water-dispersible acrylate monomer, SR415, (representing the hydrophobic "block" of the polymer), is added, and the combined phases held at 75° C. for 30 minutes before cooling the combined water phases to 60° C. The final block co-polymer solution is about 3.5% (w/w) with a 50/50 ratio of hydrophilic/hydrophobic components. The constituents of this cationic block co-polymer are shown in Table 3.

TABLE 3

| | Formulation of Water Phase Solution | | | | | |
|---|---|---|---|---|---|---|
| | WP1 | | WP2 | | WP3 | |
| Components | Water | V50 | Water | TMACEMA | Water | TMACEMA | SR415 |
| Weight (g) | 160 | 0.5 | 70 | 4 | 70 | 1.3 | 5.3 |

For the purposes of the invention, this block co-polymer is considered a "living" polymer due to the existence of free radicals on the end of each polymer. Due to the hydrophobicity, the co-polymers have the tendency to concentrate on the interface, which allow the free radicals to initiate the polymerization of acrylate monomers in the oil and water phases and to generate an acrylate shell around the microcapsules. The "living" cationic block co-polymer solution is used as the water phase in the process of microencapsulation. A total of about 0.2 g V50 can be added to the cationic block co-polymer solution as a co-initiator.

Example 2

An oil phase, containing 150 g of core oil and 21 g oil phase monomers (TBAEMA/CD9055/CN975), is preheated to 60° C. for 30 minutes under a nitrogen blanket. A water phase is added. The speed is increased to start milling to form a stable emulsion (with target size of 10 um). After 30 minutes of milling at 60° C., the batch temperature is ramped to 72° C. and held for 2 hours, and then temperature is ramped to 95° C. and held for 6 hours. Milling is continued throughout the curing cycle. In this example, all the initiators (V50 or "living" polymer) are in the water phase, while all monomers are in the oil phase, the polymerization occurs at the water-oil phase.

Example 3

An oil phase solution, containing a core oil and oil phase monomers (TBAEMA/CD9055/CN975), is preheated to 60° C. for 20 minutes, and the oil soluble initiators (Vazo 67 and 88, ~0.5% w/w of total acrylate monomers) were slowly added under a nitrogen blanket. A water phase is added to the oil phase, and the blend is milled to form a stable emulsion (at target size 10 um). After 30 minutes of milling at 60° C., the batch temperature is ramped to 72° C. and held at 72° C. for 2 hours, and then temperature is ramped to 95° C. and held at 95° C. for 6 hours. The initiators (V50 or "living" polymer) are in the water phase, while all acrylate monomers are in the oil phase.

Example 4

An oil phase, containing 150 g core oil and oil phase initiator (V67 and V88, 0.3 g each), is placed in a jacketed steel reactor at 40° C., mixing at 1000 rpm under a nitrogen blanket. The batch is preheated from to 60° C. for 45 minutes and held at 60° C. for 120 minutes for pre-initiation. 21 g of oil phase monomers (TBAEMA/CD9055/CN975) is added to the oil phase for 30 minutes of prepolymerization. The water phase is added to the oil phase, and the milling speed is increased to form a stable emulsion (at target size 10 um After 30 minutes of milling at 60° C., the batch temperature is ramped to 72° C. and held at 72° C. for 2 hours, and then temperature is ramped to 95° C. and held at 95° C. for 6 hours. In this example, the mechanism of the polymerization includes the formation of the acrylate oligomers in the oil phase, the deposition of oligomers to the oil-water interface, and the interfacial polymerization between the water-soluble "living" polymer/initiator and oil phase oligomers/monomers.

Example 5

1% polyvinyl alcohol (PVA540) solution is used as a co-emulsifier. Water phase 1 (WP1), containing 1% polyvinyl alcohol (PVA540) solution and a water phase initiator (V50), is placed in a jacketed steel reactor at 63° C., mixing at 1000 rpm under a nitrogen blanket. The batch is held at 63° C. for 60 minutes. A second water phase (WP2), containing cationic and hydrophilic acrylate monomers such as [2-(methacryloyloxy)ethyl]trimethylammonium chloride (TMACEMA), (representing the hydrophilic "block" of the polymer), is added, and the combined water phases held at 63° C. for 30 minutes. A third water phase (WP3), containing a mixture of a hydrophobic acrylate monomers such as SR206 and SR368, (representing the hydrophobic "block" of the polymer), is added, and the combined phases held at 63° C. for 30 minutes. The final block co-polymer solution is about 4.2% (w/w) with 50/50 ratio of hydrophilic/hydrophobic components. The formula of this cationic block co-polymer is shown in Table 4.

TABLE 4

| | Formulation of Water Phase Solution | | | | | |
|---|---|---|---|---|---|---|
| | WP1 | | | | WP3 | |
| | 1.2% PVA | | WP2 | | | |
| Components | solution | V50 | Water | TMACEMA | Water | SR206 | SR368 |
| Weight (g) | 250 | 0.5 | 50 | 5 | 0 | 2.5 | 2.5 |

For the purposes of the invention, this block co-polymer is considered a "living" polymer due to the existence of free radicals on the end of each polymer. Due to the hydrophobicity of WP3, milling is continued throughout the process. The "living" cationic block co-polymer solution is used as the water phase in the process of microencapsulation.

An oil phase, containing 170 g core oil and oil phase initiator (V67 0.6 g each), is placed in a jacketed steel reactor at 63° C., mixing at 1000 rpm under nitrogen. The batch is held at 60° C. for 100 minutes for pre-initiation. A total of 21.5 g of oil phase monomers (TBAEMA/SR206/SR368) is added to the oil phase over 20 minutes for prepolymerization. A water phase is added to the oil phase, and the speed is increased to form a stable emulsion (at target size 10 um). Milling is done at 63° C. for 30 minutes, the batch temperature is held at 63° C. for 3 hours, and then temperature is ramped up to 85° C. and held at 85° C. for 12 hours. The mechanism of the polymerization in this example includes the formation of acrylate oligomers in the oil phase, the deposition of oligomers to the oil-water interface, and interfacial polymerization between the water-soluble "living" polymer/initiator and oil phase monomers.

Example 6

1% polyvinyl alcohol (PVA540) solution is used as a co-emulsifier. Water phase 1, containing 1% polyvinyl alcohol (PVA540) solution, water phase initiator (V501) and 1 ml of 21.5% NaOH, is placed in a jacketed steel reactor at 63° C. with mixing at 1000 rpm under a nitrogen blanket. The batch is held at 63° C. for 60 minutes. A second water phase, containing anionic hydrophilic acrylate monomers, 2-sulfoethyl methacrylate, with the addition of 1 ml of 21.5% NaOH, (representing hydrophilic "block" of the polymer), is added, and the combined water phases are held at 63° C. for 30 minutes. A third water phase, containing a mixture of a hydrophobic acrylate monomer such as SR206 and SR368, (representing the hydrophobic "block" of the polymer), is added, and the combined phases held at 63° C. for 30 minutes. The final block co-polymer solution is about 4.2% (w/w) with 50/50 ratio of hydrophilic/hydrophobic components. The formula of this cationic block co-polymer is shown in Table 5.

TABLE 5

| | Formulation of Water Phase Solution | | | | | | | |
|---|---|---|---|---|---|---|---|---|
| | WP1 | | | WP2 | | | WP3 | |
| Components | 1.2% PVA solution | V50 | 21.5% NaOH | Water | 2-sulfoethyl methacrylate | 21.5% NaOH | Water | SR206 | SR368 |
| Weight (g) | 250 | 0.5 | 0.6 | 50 | 5 | 5 | 0 | 2.5 | 2.5 |

For the purposes of the invention, this block co-polymer is considered a "living" polymer due to the existence of free radicals on the end of each polymer. Milling is required throughout the process. The "living" anionic block co-polymer solution is used as the water phase tin the process of microencapsulation.

An oil phase, containing 170 g core oil and oil phase initiator (V67 0.6 g each), is placed in a jacketed steel reactor at 63° C., mixing at 1000 rpm under a nitrogen blanket. The batch is held at 60° C. for 100 minutes for pre-initiation. A total of 21.5 g of oil phase monomers (TBAEMA/SR206/SR368) are added to the oil phase for 20 minutes pre-polymerization. A water phase is added to the oil phase, and the speed is increased to form a stable emulsion (target size 10 um). Milling is done at 63° C. for 30 minutes, the batch temperature is held for 3 hours, and then temperature is ramped to 85° C., and held at 85° C. for 12 hours. In this example, the mechanism of the polymerization includes the formation of the acrylate oligomers in the oil phase, the deposition of oligomers to the oil-water interface, and the interfacial polymerization between the water-soluble "living" polymer/initiator and oil phase oligomers/monomers.

Example 7

Characterization of the Properties of Microcapsules

The median volume-weighted particle size of the microcapsules: The particle size is measured using an Accusizer 780A, made by Particle Sizing Systems, Santa Barbara Calif., or equivalent. The instrument is calibrated from 0 to 300 μm (micrometer or micron) using particle size standards (as available from Duke/Thermo-Fisher-Scientific Inc., Waltham, Mass., USA). Samples for particle size evaluation are prepared by diluting about 1 g of microcapsules slurry in about 5 g of de-ionized water and further diluting about 1 g of this solution in about 25 g of water. About 1 g of the most dilute sample is added to the Accusizer and the testing initiated using the autodilution feature. The Accusizer should be reading in excess of 9200 counts/second. If the counts are less than 9200 additional sample should be added. Dilute the test sample until 9200 counts/second and then the evaluation should be initiated. After 2 minutes of testing the Accusizer will display the results, including the median volume-weighted particle size. Particle sizes stated herein on a volume weighted basis are to be understood as median volume weighted particle sizes, ascertainable by the above procedure.

Characterization of free oil in microcapsule suspension: 1 g of the microcapsule suspension (40% solid) is mixed with 10 ml of hexane/DBP solution by using the automated volume dispenser to leach the free oil from microcapsule suspension, and then sited on the counter for 30 minutes. 1 ml of top, clear Hexanes/DBP layer is carefully pipetted, and measured by Agilent 6890N Gas Chromatograph (GC) to determine the free oil in suspension. The free oil results are shown in Table 6 below:

TABLE 6

| Example | 2 | 3 | 4 | 5 | 6 |
|---|---|---|---|---|---|
| Size (micron) | 11.5 | 11.6 | 12.3 | 16.3 | 15.9 |
| Free Oil (%) | 0.7 | 0.7 | 0.7 | 0.1 | 0 |

The final size of all the samples are closed to target size (10 micron), and the low free oil of all the tested samples also indicates a successful microencapsulation process which can encapsulate core materials highly efficiency with extremely low leakage.

Figure 2:
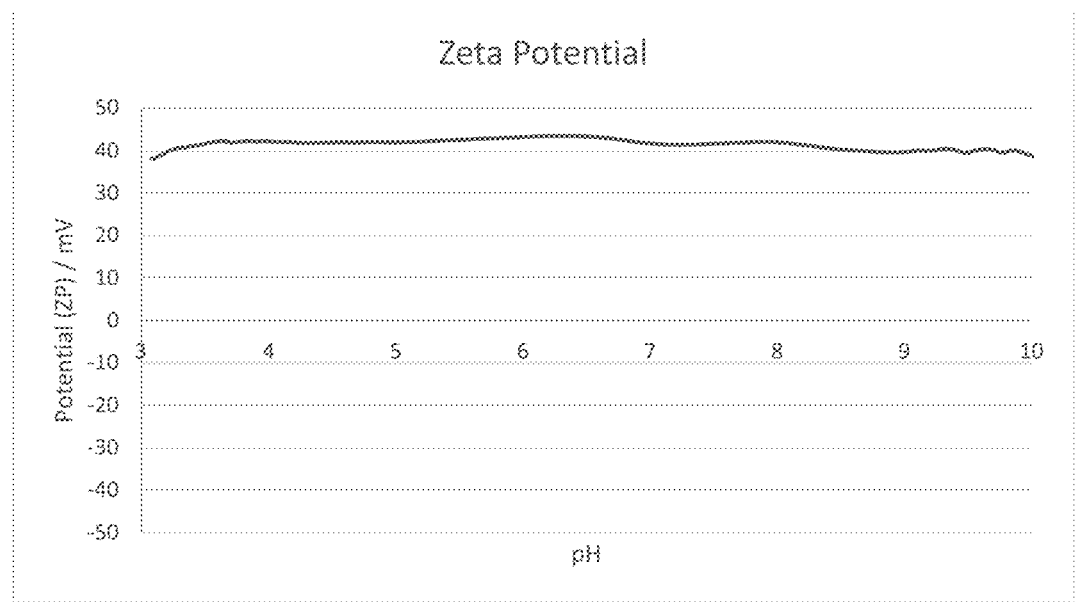
FIG. 2 is a graph of zeta potential of the microcapsules according to Example 3.
Figure 3:
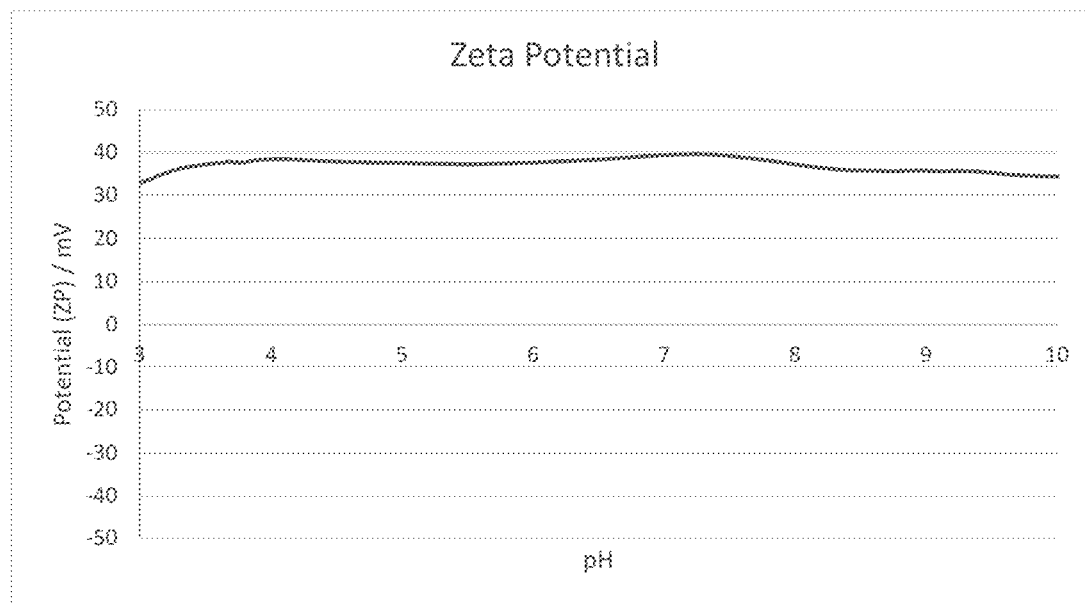
FIG. 3 is a graph of zeta potential of the microcapsules according to Example 4.
Figure 4:
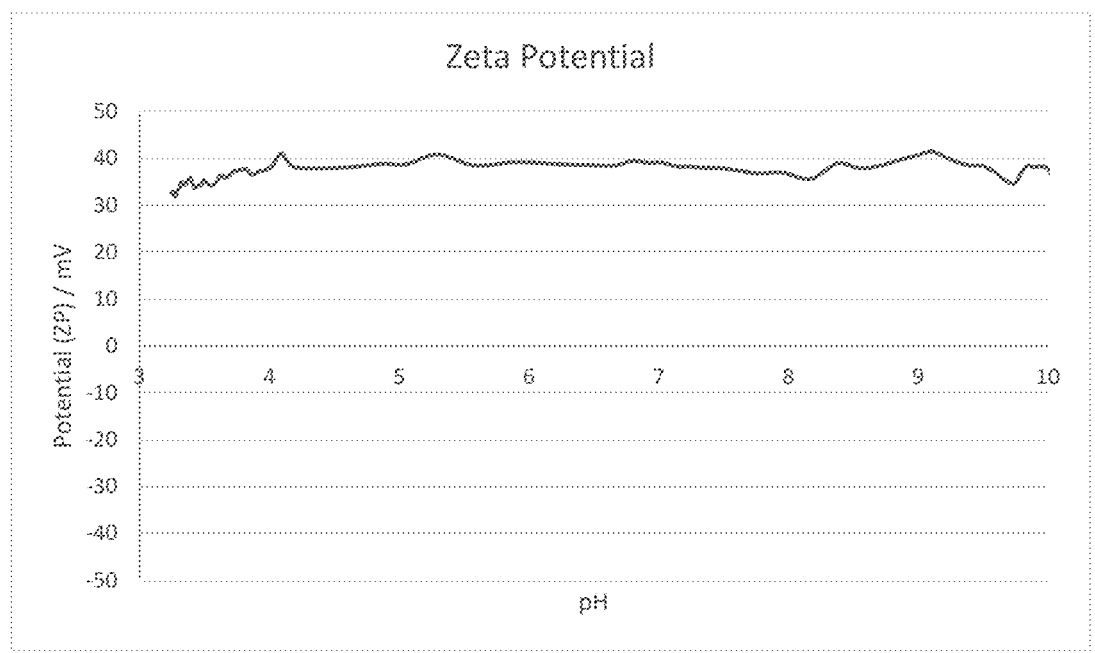
FIG. 4 is a graph of zeta potential of the microcapsules according to Example 5.
Figure 5:
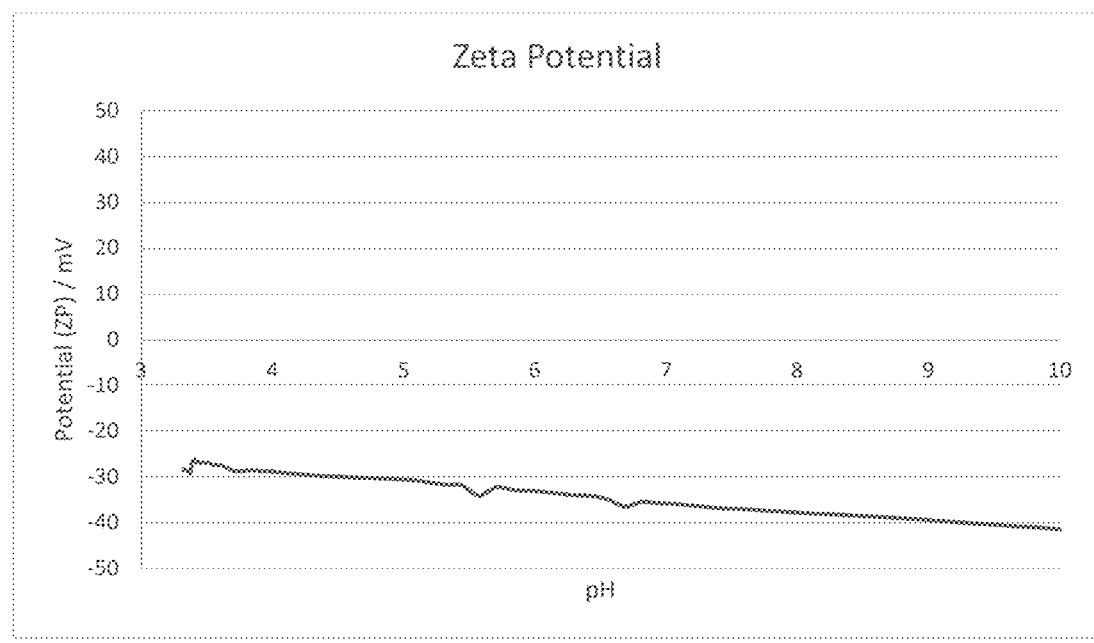
FIG. 5 is a graph of zeta potential of the microcapsules according to Example 6.

Characterization of surface charge of microcapsule samples: 10 g of microcapsule aqueous suspension (4% solid) is added in a well-cleaned sample cup, and the pH is adjusted to 10 by 0.1N NaOH. The pH of aqueous suspension is slowly adjusted from 10 to 3 by using 0.1N HCl with 10 ul/min, and the surface charge of microcapsule samples is measured by Microtrac Stabino Particle Charge Titration Analyzer and shown in FIGS. 1-5 (representing examples 2-6). The test results exhibit that the microcapsules samples can have permanent charge on their surface area, and more important, the surface charge can be tailored by using different acrylic monomer with charge functional group. The sample 1 and 2 has cationic surface charge due to the trimethylammonium group from 2-(methacryloyloxy)ethyl trimethylammonium chloride, and the sample 3 has anionic surface charge due to the sulfate group from 2-sulfoethyl methacrylate.

What we claim is:

1. A composition comprising a microcapsule comprising a core material and a shell that surrounds the core material, the core material comprising a benefit agent, the shell comprising a reaction product of at least one amphiphilic block prepolymer, the shell having an external surface having a cationic or anionic charge, and the external surface having hydrophilic functional groups, the microcapsule made by a process comprising:
   i) pre-reacting one or more water phase monomers to form an amphiphilic block polymer by the steps comprising:
      a.) dissolving or dispersing one or more free radical initiators in a first water phase to provide a source of free radicals upon activation;
      b.) dissolving or dispersing in a second water phase, one or more water soluble (meth)acrylate monomers having a hydrophilic functional group;
      c.) combining the first water phase with the second water phase and activating the initiator to form free radicals of the initiator and to pre-react the monomers forming a first prepolymer, the first prepolymer having active free radical end groups;
      d.) dispersing in a third water phase, a water insoluble but water dispersible multifunctional(meth)acrylate monomer having hydrophobic segments, the multifunctional (meth)acrylate monomer having a hydrophilicity index of at least 30, and optionally an additional water soluble (meth)acrylate monomer;
      e.) combining the first prepolymer with the multifunctional monomer of the third water phase;
      f.) heating the combined first prepolymer and the multifunctional monomer, thereby forming a polymer by free radical polymerization of the first prepolymer and the multifunctional monomer, the resulting polymer being a block polymer, the block polymer having end groups comprising a free radical,
      wherein the free radical groups of the block polymer promote chain growth of the block polymer increasing the molecular weight of the block polymer during the heating step;
      said block prepolymer being amphiphilic with hydrophobic segments and hydrophilic functional groups;
      wherein, the block polymer hydrophobic segments and increasing molecular weight decrease solubility of the block polymer precipitating the block polymer out of the water phase,
   ii) pre-reacting one or more oil phase monomers to form an amphiphilic prepolymer by steps comprising:
      a.) providing an oil phase comprising a benefit agent core material, and at least one oil soluble multifunctional (meth)acrylate monomer, having a hydrophilicity index of 20 or less and wherein from 0 to 100% by weight of the oil phase monomers comprise an oil soluble or dispersible hydrophilic (meth)acrylate monomer have a hydrophilic functional group;
      b.) heating to pre-react the monomers of the oil phase forming an oil phase prepolymer which is amphiphilic; and,
   iii) forming an emulsion by steps comprising:
      b.) emulsifying the oil phase into the water phase using high shear agitation to form an emulsion of droplets of the oil phase of less than 100 microns dispersed in the water phase;
      b.) further reacting the emulsion of the oil phase and water phase by heating the emulsion for a time and temperature, or by actinic irradiation, sufficient to form a microcapsule shell at interfaces of the oil droplets and water of the emulsion, said microcapsule shell surrounding the benefit agent core material and said microcapsule shell having a surface charge and having one or more hydrophilic functional groups.

2. The claim according to claim 1 wherein the hydrophilic functional group of the water soluble (meth)acrylate monomer of the second water phase is selected from the group consisting of hydroxy, phosphate, carboxy, amine, sulfonic and quaternary ammonium.

3. The claim according to claim 1 wherein the hydrophilic functional group of the oil phase (meth)acrylate monomer is selected from the group consisting of hydroxy, phosphate, carboxy, amine, sulfonic and quaternary ammonium.

4. The composition according to claim 1 wherein, the microcapsule has a zeta potential, measured at a pH or 7, of from +70 to −70.

5. The composition according to claim 1 wherein the various heating steps to activate the initiators and for polymerization are carried out under an inert or nitrogen blanket.

6. The composition according to claim 1 wherein the oil phase includes, in addition, one or more additives consisting of an initiator and/or a water soluble dispersible emulsifier.

7. The composition according to claim 1 wherein the first water phase initiator is activated by heating.

8. The composition according to claim 1 wherein the hydrophilic functional groups on the surface of the microcapsule shell are polar.

9. The composition according to claim 1 wherein the block prepolymer of the combined water phases is functional as an emulsifier.

10. The composition according to claim 1 wherein the prepolymer hydrophilic segments reduce oil solubility of the prepolymer thereby moving the prepolymer toward an oil-water interface of the emulsion droplets.

11. The composition according to claim 1 wherein the water phase monomer is selected from the group of monomers consisting of ethoxylated (20) trimethylolpropane triacrylate, ethoxylated (9) trimethylolpropane triacrylate, polyethylene (200) glycol dimethacrylate, polyethylene glycol (200) diacrylate, polyethylene glycol (400) diacrylate, polyethylene glycol (600) diacrylate, tris (2-hydroxy ethyl) isocyanurate triacrylate, ethoxylated (30) BPA diacrylate, ethoxylated (10) bisphenol A dimethacrylate, ethoxylated (10) bisphenol A diacrylate and ethoxylated (15) trimethylolpropane triacrylate.

12. The composition according to claim 1 wherein the oil phase monomer is selected from the group of monomers consisting of trimethylolpropane triacrylate, trimethylolpropane trimethacrylate, pentaerythritol triacrylate, pentaerythrtol tetraacrylate, di-trimethylolpropane tetraacrylate, dipentaerythritol pentaacrylate, ethoxylated (2) bisphenol A dimethacrylate, ethoxylated (3) bisphenol A diacrylate, ethoxylated (4) bisphenol A diacrylate, ethoxylated (4) bisphenol A dimethacrylate, dipropylene glycol diacrylate and ethylene glycol dimethacrylate.

13. The composition according to claim 1 wherein the core material of the microcapsule comprises from 70% to 90% by weight of the microcapsule, and the shell comprises from 10% to 30% by weight of the microcapsule.

14. The composition according to claim 1 wherein at least one water phase multifunctional (meth)acrylate monomer is selected to have a hydrophilicity index of at least 25.

15. The composition according to claim 1 wherein at least one oil phase monomer is selected to have a hydrophilicity index of less than 25.

16. The composition according to claim 1 wherein the microcapsules are cationic.

* * * * *